US009433219B2

United States Patent
Rolshausen et al.

(10) Patent No.: US 9,433,219 B2
(45) Date of Patent: Sep. 6, 2016

(54) FUNGI ANTAGONISTIC TO XYLELLA FASTIDIOSA

(75) Inventors: Philippe Rolshausen, Riverside, CA (US); Mary Caroline Roper, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/452,058

(22) Filed: Apr. 20, 2012

(65) Prior Publication Data

US 2012/0282233 A1 Nov. 8, 2012

Related U.S. Application Data

(60) Provisional application No. 61/477,537, filed on Apr. 20, 2011.

(51) Int. Cl.

| | | |
|---|---|---|
| *A01N 43/16* | (2006.01) | |
| *A01N 63/04* | (2006.01) | |
| *C07D 493/04* | (2006.01) | |
| *C12N 1/14* | (2006.01) | |
| *A01N 43/90* | (2006.01) | |

(52) U.S. Cl.
CPC ............... *A01N 63/04* (2013.01); *A01N 43/90* (2013.01)

(58) Field of Classification Search
CPC ........ C07D 493/04; C12N 1/20; C12N 1/14; C12R 1/025; A01N 43/16; A01N 43/90; A01N 2300/00; A01N 63/00–63/04; A01N 65/00
See application file for complete search history.

(56) References Cited

U.S. PATENT DOCUMENTS

| | | | | |
|---|---|---|---|---|
| 3,558,658 A | * | 1/1971 | McIntyre | 549/282 |
| 6,143,312 A | * | 11/2000 | Gohbara et al. | 424/408 |
| 2001/0014324 A1 | * | 8/2001 | Moesinger | 424/115 |
| 2008/0090729 A1 | * | 4/2008 | Banerjee et al. | 504/101 |
| 2009/0143230 A1 | * | 6/2009 | Melander et al. | 504/276 |

FOREIGN PATENT DOCUMENTS

JP 42011997 B4 * 7/1967

OTHER PUBLICATIONS

Hiromitsu Nakajima, Tatsuaki Ishida, Yuzuru Otsuka, Takashi Hamasaki and Masakatsu Ichinoe, Phytotoxins and Related Metabolites Produced by Bipolaris Coicis, The Pathogen of Job's Tears, 1997, Phytochemistry, vol. 45, No. 1, pp. 41-45.*

M. Solfrizzo, A. De Girolamo, C. Vitti, K. Tylkowska, J. Grabarkiewicz-Szczesna, D. Szopinska, & H. Dorna, Toxigenic profile of Alternaria alternata and Alternaria radicina occurring on umbelliferous plants, 2005, Food Additives and Contaminants, Apr. 2005; 22(4): 302-308.*

Blake Bextine, David Lampe, Carol Lauzon, Brian Jackson, Thomas A. Miller, Establishment of a Genetically Marked Insect-Derived Symbiont in Multiple Host Plants, 2005, Current Microbiology vol. 50, pp. 1-7.*

(Continued)

*Primary Examiner* — Ralph Gitomer
*Assistant Examiner* — Trent Clarke
(74) *Attorney, Agent, or Firm* — Joseph R. Baker, Jr.; Gavrilovich, Dodd & Lindsey LLP

(57) ABSTRACT

The disclosure describes fungal organisms and preparations useful for inhibiting infection by *Xylella* sp. and in the treatment of Pierce's Disease.

8 Claims, 2 Drawing Sheets

(56) References Cited

OTHER PUBLICATIONS

Moon J. Kim, Elizabeth Bancroft, Eleanor Lehnkering, Rodney M. Donlan, and Laurene Mascola, Alcaligenes xylosoxidans Bloodstream Infections in Outpatient Oncology Office, 2008, Emerging Infectious Diseases, vol. 14, No. 7, pp. 1046-1052.*

NPL pdf document "Guidance memorandum Mar. 4, 2014" accessed Mar. 27, 2014 from http://www.uspto.gov/patents/law/exam/myriad-mayo_guidance.pdf.*

NPL pdf document "*Curvularia* sp.", screenprint of Curvularia webpage from Mycology Online from the University of Adelaide http://www.mycology.adelaide.edu.au/Fungal_Descriptions/Hyphomycetes_(dematiaceous)/Curvularia/?template=print accessed Sep. 22, 2014.*

Strijewski, Spassov, Kemmer, Vlahov and Snatzke, Tertiary Acetates Controlling the Mycotoxin Production of Curvularia Lunata, 1982, Biotechnology Letters, vol. 4, No. 8, pp. 495-500.*

Ying-lao Zhang, Li-chun Kong, Dong-hua Jiang, Cai-ping Yin, Qi-min Cai, Qiong Chen, Jiang-yan Zheng, Phytotoxic and antifungal metabolites from *Curvularia* sp. FH01 isolated from the gut of Atractomorpha sinensis, 2011, Bioresource Technology, vol. 102, pp. 3575-3577, published online Oct. 13, 2010.*

\* cited by examiner

FUNGI ANTAGONISTIC TO XYLELLA FASTIDIOSA

CROSS REFERENCE TO RELATED APPLICATIONS

This application claims priority from U.S. Provisional Application Ser. No. 61/477,537, filed Apr. 20, 2011, which is incorporated herein by reference.

FIELD OF THE INVENTION

The invention relates generally to methods and compositions useful for treating plant diseases, in particular infections by pathogens.

BACKGROUND

*Xylella fastidiosa* (Xf) is a xylem limited bacterium that dwells in a wide array of plant species and the foregut of certain xylem feeding insects. The insects serve to transport Xf from plant to plant when feeding. Xf does not harm its host insect and most plant hosts are not harmed by Xf. However certain plant species are susceptible to strains of Xf and disease can occur.

SUMMARY

The disclosure provides a method for preventing infection and/or protecting plants from infection by *Xylella fastidiosa* microorganisms comprising inoculating the plant with a fungal organism selected from the group consisting of *Cochliobolus* sp., *Aspergillus* sp., *Paeosphaeria* sp., *Ulocladium* sp., *Dicostroma* sp., *Geomyces* sp., and *Cryptococcus* sp., and one baceterial organism *Achromobacter* sp.

The disclosure provides a method for preventing infection and/or protecting a plant from infection by *Xylella* sp. microorganisms comprising inoculating the plant with (i) an anti-Xf endophytic microorganism selected from the group consisting of *Cochliobolus* sp., *Aspergillius* sp., *Phaeosphaeria* sp., *Ulocladium* sp., *Dicostroma* sp., *Geomyces* sp., *Achromobacter* sp. and *Cryptococcus* sp., and any combination thereof; and/or (ii) an extract comprising an anti-Xf agent that inhibits *Xylella* sp. infection. In one embodiment, the *Xylella* sp. is *Xylella fastidiosa*. In another embodiment, the anti-Xf endophytic microorganism *Achromobacter* sp. or *Geomyces* sp. In yet another embodiment, the anti-Xf endophytic microorganism comprises a combination of *Achromobacter* sp. and *Geomyces* sp. In yet another embodiment, the plant is a monocotyleyledonous plant. In one embodiment, the plant is a dictotyledonous plant. In yet another embodiment, the plant is selected from the group consisting of grape, oleander, oak, almond, peach, pear, citrus, coffee, maple, mulberry, elm, sycamore, and alfalfa. In one embodiment, the anti-Xf endophytic microorganism is inoculated in the xylem of the plant. In yet another embodiment, the anti-Xf agent comprises the general structural formula selected from the group consisting of: (a) Formula Ia:

(Formula Ia)

wherein, $R^2$ is selected from the group comprising halo, CN, O, OH, NH, $NH_2$, S, SH, and $CH_2$;

$R^3$-$R^4$ are each individually selected from the group comprising H, halo, hydroxyl, cyano, thiol, amino, optionally substituted ($C_1$-$C_6$)alkyl, and optionally substituted ($C_1$-$C_6$)alkenyl; and $R^6$ is selected from the group comprising H, optionally substituted ($C_1$-$C_6$)alkyl, and optionally substituted ($C_1$-$C_6$)alkenyl, and optionally substituted heterocycle;

(b) Formula Ib:

(Formula Ib)

wherein, $R^2$ is selected from the group comprising halo, CN, O, OH, NH, $NH_2$, S, SH, and $CH_2$;

$R^3$ is individually selected from the group comprising H, halo, hydroxyl, cyano, thiol, amino, optionally substituted ($C_1$-$C_6$)alkyl, and optionally substituted ($C_1$-$C_6$)alkenyl; and $R^6$ is selected from the group comprising H, optionally substituted ($C_1$-$C_6$)alkyl, and optionally substituted ($C_1$-$C_6$) alkenyl, and optionally substituted heterocycle;

(c)

(Radicinin)

(acetyl-radicinin)

(Deoxy-radicinin)

and (2S,3S,4S-radicinol)

(2S,3S,4S-epi-radicinol)

In one embodiment, the anti-Xf agent is administered by a syringe into the xylem.

The disclosure also provides a composition for carrying out the methods above, wherein the composition comprises at least one anti-Xf endophytic microorganism and/or at least one anti-Xf agent. In another embodiment, the at least one substantially purified anti-Xf endoyphtic microorganism is selected from the group consisting of *Cochliobolus* sp., *Aspergililus* sp., *Phaeosphaeria* sp., *Ulocladium* sp., *Dicostroma* sp., *Geomyces* sp., *Achromobacter* sp. and *Cryptococcus* sp. and any combination thereof. In another embodiment, the composition is an aqueous media. In one embodiment, the composition comprises an anti-Xf agent having the general structural formula selected from the group consisting of: (a) Formula Ia:

(Formula Ia)

wherein, $R^2$ is selected from the group comprising halo, CN, O, OH, NH, $NH_2$, S, SH, and $CH_2$;

$R^3$-$R^4$ are each individually selected from the group comprising H, halo, hydroxyl, cyano, thiol, amino, optionally substituted ($C_1$-$C_6$)alkyl, and optionally substituted ($C_1$-$C_6$)alkenyl; and $R^6$ is selected from the group comprising H, optionally substituted ($C_1$-$C_6$)alkyl, and optionally substituted ($C_1$-$C_6$)alkenyl, and optionally substituted heterocycle;

(b) Formula Ib:

(Formula Ib)

wherein, $R^2$ is selected from the group comprising halo, CN, O, OH, NH, $NH_2$, S, SH, and $CH_2$;

$R^3$ is individually selected from the group comprising H, halo, hydroxyl, cyano, thiol, amino, optionally substituted ($C_1$-$C_6$)alkyl, and optionally substituted ($C_1$-$C_6$)alkenyl; and $R^6$ is selected from the group comprising H, optionally substituted ($C_1$-$C_6$)alkyl, and optionally substituted ($C_1$-$C_6$) alkenyl, and optionally substituted heterocycle;

(c)

(Radicinin)

(acetyl-radicinin)

(Deoxy-radicinin)

(2S,3S,4S-radicinol)

(2S,3S,4S-epi-radicinol)

DETAILED DESCRIPTION

Figure 1A:
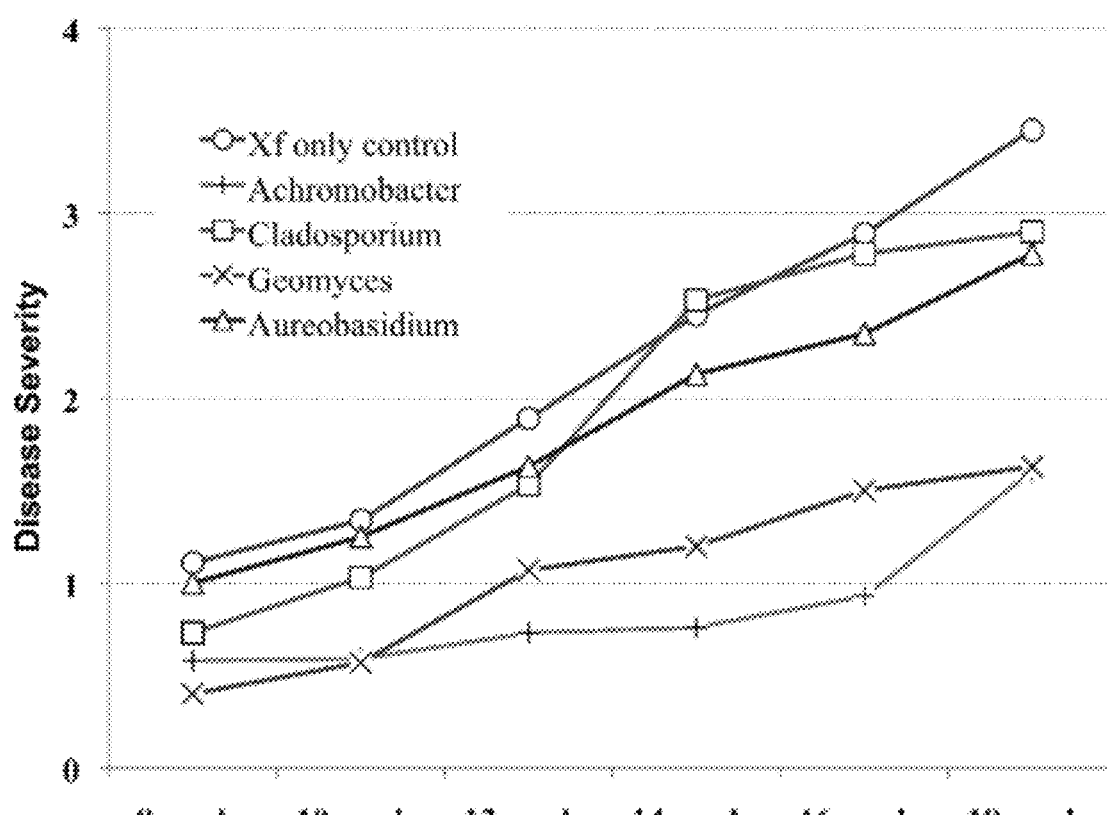
FIG. 1A-B show inhibition of *Xylella fastidiosa* with different fungal cultures. A) Both *Geomyces* sp. and *Achromobacter* sp. suppressed PD development in grapevine cuttings cv. 'Merlot' mechanically inoculated with Xf. Following inoculation, plants were rated weekly on a 0-5 disease scale with 0=healthy and 5=dead. B) *Geomyces* sp., *Achromobacter* sp., and *Aureobasidium* sp. caused a reduction in Xf titer as compared to plants inoculated with Xf alone.
Figure 1B:
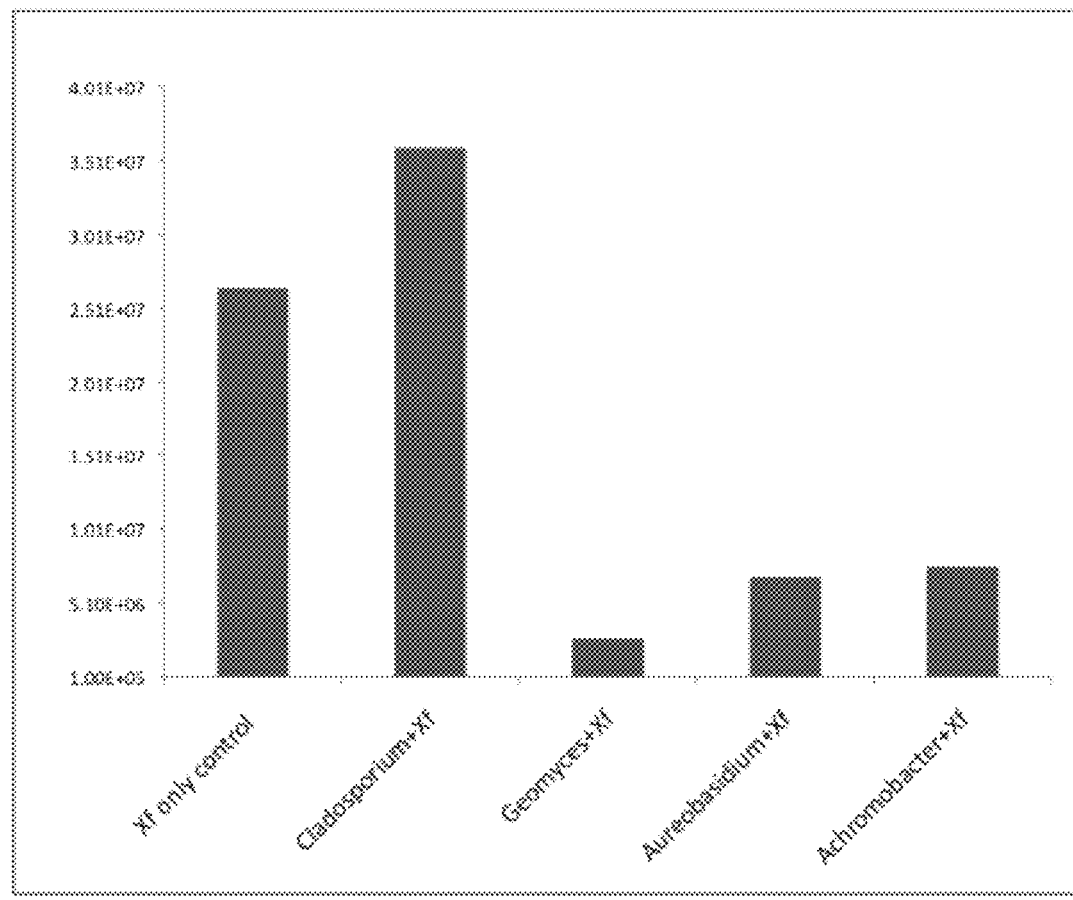

As used herein and in the appended claims, the singular forms "a," "and," and "the" include plural referents unless the context clearly dictates otherwise. Thus, for example, reference to "a plant" includes a plurality of such plants and reference to "the pathogen" includes reference to one or more pathogens known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

Crop infestations can cause severe damage to crop production and can cause severe economic harm to farmers and consumers. One bacterium responsible for plant infections is *Xylella*, such as *Xylella fastidiosa* (Xf). *Xylella fastidiosa* is a gram-negative, xylem-limited bacterium capable of affecting economically important crops. The bacterium has a large host range, including at least 28 families of both monocotyleyledonous and dictotyledonous plants. Plant hosts for *X. fastidiosa* include miscellaneous ornamentals, grape, oleander, oak, almond, peach, pear, citrus, coffee, maple, mulberry, elm, sycamore, and alfalfa, where the bacterium inhabits the plants' xylem. Other strains of *Xylella* cause important diseases of peach, citrus, coffee, and numerous forest tree species. Vectors, such as insects like xylem sap-feeding sharpshooters, acquire the bacterium by feeding on infected plants and subsequently infect other plants. *Xylella* can also be graft transmitted.

Pierce's Disease (PD) is caused by the bacterium *Xylella fastidiosa* and is spread by certain kinds of sharpshooters known as sharpshooters. The bacterium resides in the xylem. Insects that feed on xylem sap transmit the bacteria from diseased to healthy plants and thus are the vector for spread of the disease and bacteria. Plants (e.g., grapevines) shows symptoms of bacterial and infection when the bacteria block the water conducting system and reduce the flow of water to the leaves. The first evidence of PD infection usually is a drying or "scorching" of leaves. About mid-growing season, when foliar scorching begins, some or all of the fruit clusters may wilt and dry up. The bark on affected canes often matures unevenly, leaving islands of mature (brown) bark surrounded by immature (green) bark or the reverse. Environmental stress (e.g., drought) hastens an infected plant's demise.

Pierce's Disease occurs in North America through Central America and has been reported in some parts of northwestern South America and is common in some California vineyards every year, with the most dramatic losses occurring in the Temecula Valley, Coachella Valley, Napa Valley and in parts of the San Joaquin Valley. Economic damages from the disease have been estimated to cost as much as $20,000 per acre. During severe epidemics, losses to PD may require major replanting. Currently there are more than 500 million commercial grapevines in the United States, with 40% of the acreage at risk for significant economic loss. Outbreak of Pierce's Disease in California has also had a major impact on the state's nursery business due to quarantines imposed in efforts to prevent the spread of the disease.

The manifestation of disease is related to at least two parameters: (1) the successful multi-directional dissemination of Xf within the plant and (2) the plant phenotype that allows a particular strain of Xf to reach high populations within it. These parameters are associated and largely determine whether a particular strain of Xf will be a harmless entophyte or a pathogen in any given plant. Plant phenotype and the level of affinity each strain of Xf has for a particular plant species/strain are the primary factors relating to the disease causing threshold.

Dissemination of Xf within plants is by three modes: Horizontal movement by secreting pectin degrading enzymes to breaks down the pith membrane of xylem vessel walls allowing Xf to disseminate into adjacent xylem vessels. Xf is also carried along in the xylem flow to disseminate upward, e.g., away from the roots. The final mode of dissemination is for Xf to crawl against the flow of xylem. Xf uses minute tentacles (phili) to preferably and arduously migrate against the flow of xylem. This mode of dissemination is used by the bacterium to colonize the enduring regions of the plant, e.g., lower branches, trunk, and roots and thereby help insure the survival of Xf.

Once Xf colonizes the enduring regions of the plant such as the trunk, the infection tends to become chronic. Conversely Xf does not, of necessity, create a chronic infection when it infects a plant. If the bacterium does not achieve colonization of enduring regions of the plant and is limited to the green parts such as the canes that are pruned after harvest then the infection is removed.

Since the mid-1970s, other strains of *Xylella fastidiosa* have been discovered, and almost all of these cause leaf scorching of woody perennials, such as American elm, maple, mulberry, or plum. In some plants, such as peach and alfalfa, the bacterium slows and stunts plant growth. *Xylella* sp., such as *Xylella fastidiosa*, are responsible for variegated chlorosis in citrus, almond leaf scorch disease, phony peach disease, alfalfa dwarf, and others. *Xylella fastidiosa* attacks citrus fruits by blocking the xylem, resulting in juiceless fruits of no commercial value.

Methods of treating or preventing infection by *Xylella* which have been tried include control of the insect vectors (such as through pesticide and use or physical barriers), destruction of infected plants, and pruning and freezing. Other methods contemplated include the use of other bacterial species and bacteriophages, for the control of *Xylella fastidiosa* in host plants, the use of broad-spectrum antibiotics or boosting levels of essential plant bacterial micronutrients such as zinc, iron, copper, and molybdenum that could be toxic to *Xylella* sp. For example, U.S. Patent Application Publication No. 20050053584, describes the use of a benign strain of Xf (EB92-1) to inhibit a virulent strain of Xf. This form of bio-control can be referred to as "competitive displacement." The deployment of competitive displacement is problematic, however, because the characteristics that make a particular strain virulent tend to give the virulent strain competitive advantage over the benign strains. Virulence by any one Xf strain is not universal to all plants that it infects; rather it is determined by the success of a particular Xf strain in its specific species/strain of host plant. Thus, when a strain of Xf comes to resides in its preferred plant host any benign strains of Xf that cohabitates the plant are at competitive disadvantage. The pre-establishment of the benign strain of Xf in the target plant may offset the benign strains disadvantage. This "head start advantage" tends to weaken over time and eventually the benign strain will yield to the aggressive strain. Thus, it may be required to reapply the benign strain after three to five years.

Yet another way to prevent the infection is by genetically modifying the chemistry and structure of the xylem making it uninhabitable for the bacteria (see, e.g., U.S. Pat. No. 6,232,528).

Control of PD with fungi or fungal metabolites is a largely unexplored research area, although fungi are known to produce an array of secondary compounds that have antimicrobial properties (Getha et al., 2009; Mathivanan et al., 2008). Indeed, using fungi as biocontrol agents against plant disease is an active area of research. Some examples include the use of Trichoderma species to control avocado white root rot, the use of Penicillium oxalicum to control powdery mildew of strawberries, and the use of fungal endophytes to control frosty pod of cacao (Cal et al. 2008; Mejia et al, 2008; Rosa and Herrera, 2009). In addition, bio-pesticides that are fungal spore-based are commercially available.

This disclosure provides microorganisms that inhibit and treat Xf infection as well as compounds that inhibit, cure and/or treat Xf infection. The microorganism and compounds were developed through a focused analysis of endophytic fungi and microorganisms in grapevines and evaluating their potential as biocontrol agents against Xf. The methods of the disclosure characterized the grapevines that escaped Pierce's Disease in natural vineyard settings, and compared the microbial population to PD-infected grapevines. Through this process fungi and bacterial microorganisms were identified that are unique to PD-escaped vines. Such fungal endophytes and bacteria possess anti-Xf properties, likely due to the production of certain metabolites. Once identified, the ability of these endophytes and their natural products were assessed for inhibitory activity against Xf in vitro.

Greenhouse tests were performed to determine if (1) the identified endophytic fungi have potential use as prophylactic bio-control agents for control by inoculating grapevine cuttings with endophytic, Xf-antagonistic fungi; and (2) if injection of fungal natural products have curative properties in PD-infected grapevines cuttings.

Seven fungi were identified that were strongly inhibitory to Xf in vitro, all of which have been identified to genus level based on ribosomal DNA sequences-*Aspergillus* sp., *Cochliobolus* sp., *Cryptococcus* sp., *Discostroma* sp., *Geomyces* sp., *Phaeosphaeria* sp., and *Ulocladium* sp. In addition, a bacterium (*Achromobacter* sp.) was identified based on 16s ribosomal DNA that strongly inhibits Xf in vitro. This bacterium has a yeast-like growth habit, and was selected for further characterization. It was only later determined to be a bacterium, but because of its strong inhibitory effects was further studied.

Fungal candidates that displayed two features: (1) showed inhibitory effect of Xf in in vitro assays; and (2) were heavily sporulating in culture were selected for additional studies. Spore formation is an important criteria in order to re-introduce these fungal endophytes into grape cuttings by vacuum filtration or other methods. Because of their small size and shape, fungal spores are more likely to infiltrate and colonize the plant xylem vessels than fungal hyphae. Fungal spores were harvested in sterile water and the concentration was adjusted to $10^5$ to $10^6$ spores/ml.

Using the methods described above and elsewhere herein, anti-Xf endophytic fungi and microorganisms were identified that are useful for treating plants having an Xf infection as well as preventing spread or infection by Xf. As used herein the term "anti-Xf endophytic microorganisms" refers to *Aspergillus* sp., *Cochliobolus* sp., *Cryptococcus* sp., *Discostroma* sp., *Ulocladium* sp., *Phaeosphaeria* sp., *Geomyces* sp. and *Achromobacter* sp.

The anti-Xf endophytic microorganisms of the disclosure and anti-Xf agents isolated therefrom are useful in the treatment of target plants to confer Xf resistance and/or treatment of infection. Suitable plants include, but are not limited to, ornamentals, grape, oleander, oak, almond, peach, pear, citrus, coffee, maple, mulberry, elm, sycamore, alfalfa, peach, and numerous forest tree species susceptible to *Xylella* sp. infection such as Xf infection. The plant may be at any stage of growth, including seeds, seedlings, or full plants. In addition, as discussed herein, any part of the plant may be inoculated; suitable plant parts include seeds, roots, leaves, flowers, stems, trunks, etc.

In one embodiment the disclosure relates to target plants obtained by artificially introducing an anti-Xf endophytic microorganisms into plants and plant parts not infected with an anti-Xf endophytic microorganisms. In the context of this disclosure, the anti-Xf endophytic microorganisms which is artificially introduced into the target plant, is a microorganism that confers Xf infection resistance to the target plant.

In a one embodiment, a pure culture of an anti-Xf endophytic microorganism is used to inoculate plants or plant parts. A "pure culture" in this context means a culture devoid of other cultured endophytic fungi. The culture may be of spores, hyphae, mycelia, or other forms of the fungi, with spores being particularly preferred. In general, spores are used at $1-5 \times 10^{3-8}$ spores per plant with $1-3 \times 10^{4-6}$ being common and $1-3 \times 10^5$ being typical. As outlined herein, the anti-Xf endophytic microorganisms of the disclosure may be cultured in a variety of ways, including the use of plates and liquid cultures.

In another embodiment, the plant may be inoculated by vacuum infiltration. In this embodiment, a stem or cutting is placed in an aqueous media comprising the anti-Xf endophytic microorganisms and a vacuum is applied to draw the aqueous media comprising the anti-Xf endophytic microorganisms into the cutting or stem. Once inoculated the cutting or stem is grown using recognized techniques. Typically this process is performed in a nursery.

The spores or other innoculum may be placed on seed coats, particularly on seeds of anti-Xf endophytic microorganisms-free seeds (either naturally occurring or treated to remove any endophytes). It should be noted that the plants, including seeds, may be inoculated with combinations of anti-Xf endophytic microorganism cultures.

In another embodiment, an extract of an anti-Xf endophytic microorganism comprising an agent that inhibits Xf growth or infection is used to treat or inhibit a *Xylella* sp infection (e.g., a Xf infection that causes PD). For example, an extract from an anti-Xf endophytic microorganism can comprise an agent that inhibits Xf growth and transmission. In this embodiment, a culture of an anti-Xf endophytic microorganism can be disrupted and crude or purified extract may be applied to the plant. In one embodiment, the extract or purified composition is administered to the plant at the site of a *Xylella* sp. growth (e.g., the trunk or stem).

For example, in one embodiment, an extract of an anti-Xf endophytic microorganism of the disclosure was prepare and purified to identify an agent that inhibits Xf growth. The agent was identified as having structural Formula I:

(Formula I)

wherein, $A^1$ and $A^2$ are each individually O, S, or NH;

$R^1$ and $R^2$ are each individually selected from the group comprising halo, CN, O, OH, NH, $NH_2$, S, SH, and $CH_2$;

$R^3$-$R^5$ are each individually selected from the group comprising H, halo, hydroxyl, cyano, thiol, amino, optionally substituted ($C_1$-$C_6$)alkyl, and optionally substituted ($C_1$-$C_6$)alkenyl; and $R^6$ is selected from the group comprising H, optionally substituted ($C_1$-$C_6$)alkyl, and optionally substituted ($C_1$-$C_6$)alkenyl, and optionally substituted heterocycle.

In a further embodiment, the disclosure provides for a compound having structural Formula Ia:

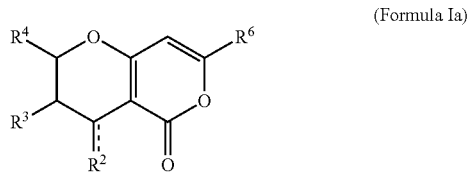

(Formula Ia)

wherein, $R^2$ is selected from the group comprising halo, CN, O, OH, NH, $NH_2$, S, SH, and $CH_2$;

$R^3$-$R^4$ are each individually selected from the group comprising H, halo, hydroxyl, cyano, thiol, amino, optionally substituted ($C_1$-$C_6$)alkyl, and optionally substituted ($C_1$-$C_6$)alkenyl; and $R^6$ is selected from the group comprising H, optionally substituted ($C_1$-$C_6$)alkyl, and optionally substituted ($C_1$-$C_6$)alkenyl, and optionally substituted heterocycle.

In another embodiment, the disclosure provides for a compound having structural Formula Ib:

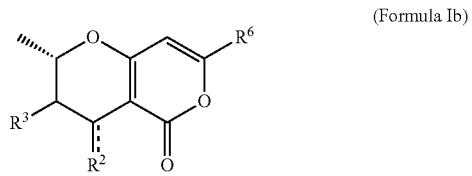

(Formula Ib)

wherein, $R^2$ is selected from the group comprising halo, CN, O, OH, NH, $NH_2$, S, SH, and $CH_2$;

$R^3$ is individually selected from the group comprising H, halo, hydroxyl, cyano, thiol, amino, optionally substituted ($C_1$-$C_6$)alkyl, and optionally substituted ($C_1$-$C_6$)alkenyl; and $R^6$ is selected from the group comprising H, optionally substituted ($C_1$-$C_6$)alkyl, and optionally substituted ($C_1$-$C_6$)alkenyl, and optionally substituted heterocycle.

In a specific embodiment, the agent is selected from the group consisting of:

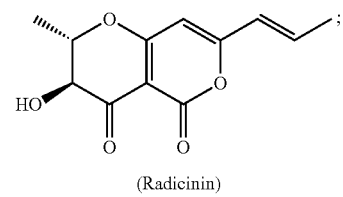

(Radicinin)

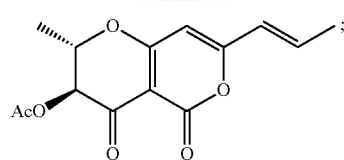

(acetyl-radicinin)

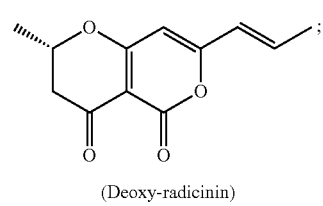

(Deoxy-radicinin)

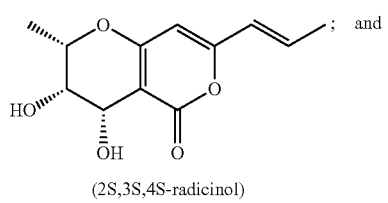

and (2S,3S,4S-radicinol)

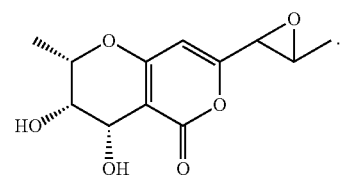

(2S,3S,4S-epi-radicinol)

As used herein an anti-Xf agent of the disclosure refers to an agent having structural Formula I:

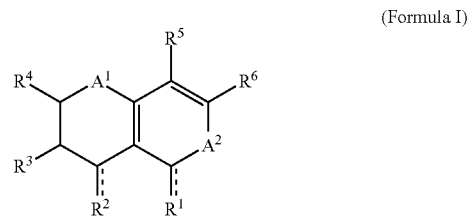

(Formula I)

wherein, $A^1$ and $A^2$ are each individually O, S, or NH;

$R^1$ and $R^2$ are each individually selected from the group comprising halo, CN, O, OH, NH, $NH_2$, S, SH, and $CH_2$;

$R^3$-$R^5$ are each individually selected from the group comprising H, halo, hydroxyl, cyano, thiol, amino, optionally substituted ($C_1$-$C_6$)alkyl, and optionally substituted ($C_1$-$C_6$)alkenyl; and $R^6$ is selected from the group comprising H, optionally substituted ($C_1$-$C_6$)alkyl, and optionally substituted ($C_1$-$C_6$-alkenyl, and optionally substituted heterocycle.

In a further embodiment, the disclosure provides for an anti-Xf agent having structural Formula Ia:

(Formula Ia)

wherein,

R² is selected from the group comprising halo, CN, O, OH, NH, NH₂, S, SH, and CH₂;

R³-R⁴ are each individually selected from the group comprising H, halo, hydroxyl, cyano, thiol, amino, optionally substituted ($C_1$-$C_6$)alkyl, and optionally substituted ($C_1$-$C_6$)alkenyl; and R⁶ is selected from the group comprising H, optionally substituted ($C_1$-$C_6$)alkyl, and optionally substituted ($C_1$-$C_6$) alkenyl, and optionally substituted heterocycle.

As used herein an anti-Xf agent of the disclosure refers to an agent having structural Formula Ib:

(Formula Ib)

wherein,

R² is selected from the group comprising halo, CN, O, OH, NH, NH₂, S, SH, and CH₂;

R³ is individually selected from the group comprising H, halo, hydroxyl, cyano, thiol, amino, optionally substituted ($C_1$-$C_6$)alkyl, and optionally substituted ($C_1$-$C_6$)alkenyl; and R⁶ is selected from the group comprising H, optionally substituted ($C_1$-$C_6$)alkyl, and optionally substituted ($C_1$-$C_6$) alkenyl, and optionally substituted heterocycle.

As used herein an anti-Xf agent of the disclosure refers to an agent selected from the group consisting of:

(Radicinin)

(acetyl-radicinin)

(Deoxy-radicinin)

(2S, 3S, 4S-radicinol)

(2S, 3S, 4S-epi-radicinol)

In one embodiment, a combination of anti-Xf agents may be used to treat an Xf infection or prevent an Xf infection.

Methods are provided for protecting a plant from a pathogen (e.g., an Xf pathogen) comprising applying an effective amount of a composition comprising an anti-Xf endophytic microorganism of the disclosure and/or an anti-Xf agent/compound of the disclosure. "Effective amount" is intended to mean an amount sufficient to control a virulent pathogen.

The compositions comprising the anti-Xf endophytic microorganism(s) and/or an anti-Xf agent of the disclosure may comprise a surface-active agent, an inert carrier, a preservative, a humectant, a feeding stimulant, an attractant, an encapsulating agent, a binder, an emulsifier, a dye, a UV protective, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pathogens. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the disclosure are normally applied in the form of compositions and can be applied to the crop area, plant, or seed to be treated. For example, the compositions of the disclosure may be applied during growth, seeding or storage.

The anti-Xf endophytic microorganism(s) and/or an anti-Xf agent of the disclosure may be applied simultaneously or in succession with other compounds. Methods of applying a composition of the disclosure include, but are not limited to, foliar application, seed coating, injection and soil application. The number of applications and the rate of application depend on the intensity of infestation by the corresponding pathogen.

Suitable surface-active agents include, but are not limited to, anionic compounds such as a carboxylate of, for example, a metal; carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions of the disclosure can be in a suitable form for direct application or as a concentrate of primary composition that requires dilution with a suitable quantity of water or other diluant before application. The concentration of benign fungal organism will vary depending upon the nature of the particular formulation, specifically, whether it is a concentrate or to be used directly.

A compositions of the disclosure can be applied to the environment of a plant pathogen by, for example, spraying, atomizing, dusting, scattering, coating, injecting or pouring, introducing into or on the soil, introducing into irrigation water, by seed treatment or general application or dusting at the time when the pathogen has begun to appear or before the appearance of pathogens as a protective measure. It is generally important to obtain good control of pathogens in the early stages of plant growth, as this is the time when the plant can be most severely damaged. The compositions of the disclosure can conveniently contain an insecticide if this is thought necessary.

In one embodiment, an anti-Xf agent of the disclosure can be injected into the trunk of a plant (e.g., a grape vine). For example, an 18-gauge syringe needle can be attached to a syringe barrel and used to pierce the base of the vine with the needle. The injection apparatus can be secured to the vine and left in place. This will allow for a continuous drip of the solution into the xylem stream of the plant—the niche where Xf dwells. This xylem infiltration technique is used by arborists to deliver insecticides, fungicides or plant growth regulators to achieve systemic translocation of the product into the xylem stream. There are several commercial products built on this concept, including SilvaShield Injectable (Bayer AG), Merit Injectable (Tree Tech, Inc.) and ChemJet Tree Injector (ChemJet).

Compositions of the disclosure find use in protecting plants, seeds, and plant products in a variety of ways. For example, the compositions can be used in a method that involves placing an effective amount of the composition in the environment of the pathogen by a procedure selected from the group consisting of spraying, dusting, broadcasting, or seed coating. The methods of the embodiments may be effective against a variety of plant pathogens.

EXAMPLES

One-year-old canes from grapevines varieties Chardonnay and Cabernet Sauvignon were sampled. Although apparently healthy, these grapevines were submitted to the constant disease pressure present in Riverside County. Canes were pressure-bombed and 100 μl of the sap was plated on general fungal medium, Potato Dextrose Agar (PDA), amended with tetracycline to inhibit bacterial growth. After 2 weeks of growth at room temperature, the fungi growing were transferred to fresh PDA medium in order to obtain pure cultures. Fungal DNA was extracted from these pure cultures with a Qiagen DNA extraction kit. Following this, the ribosomal DNA was PCR-amplified (600 base pairs) and sequenced (forward and reverse). Fungal taxa were identified after comparing the r-DNA sequence to homologous sequences posted in the GenBank database. Taxa were identified from the sap of these vines, and included *Aureobasidium, Cladosporium, Cryptococcus, Cochliobolus* and *Chaetomium.*

Samples were also obtained from four varieties in two vineyards in Napa County and one vineyard in Riverside. Grapevine varieties included Chardonnay, Merlot, Riesling and Cabernet Sauvignon. One-year-old canes were collected including the wood spur from blocks that had both diseased and PD-escaped grapevines. Samples were pressure-bombed to extract the xylem sap. Following extraction, 100 μl of the xylem sap was plated on general fungal medium, Potato Dextrose Agar (PDA), amended with tetracycline to inhibit bacterial growth. In addition, wood chips were excised from the one-year-old cane and spur and were also plated on PDA-tetracycline medium. Fungi were cultured and identified as described above. The list of endophytic fungi present in escaped and diseased grapevines is presented in Table 1. *Cladosporium* and *Aureobasidium* were present in all grapevine varieties and were also found in the xylem sap.

TABLE 1

Identification and percent recovery of fungal taxa from PD-escaped and PD-infected grapevines. Results are based on sampling from 3 vineyards in Napa and Riverside County, and include 4 grapevine varieties (Merlot, Cabernet Sauvignon, Chardonnay, Riesling). Fungi were isolated from xylem sap and one-year-old cane and spur wood.

| | Percent Recovery | |
|---|---|---|
| Fungal Taxa | Escaped Grapevines (n = 37) | Diseased Grapevines (n = 30) |
| *Cladosporium* sp. | 63 | 57 |
| *Aureobasidium* sp. | 59 | 60 |
| *Alternaria* sp. | 11 | 30 |
| *Cryptococcus* sp. | 14 | 7 |
| *Penicillium* sp. | 3 | 3 |
| *Geomyces* sp. | 3 | 7 |
| *Biscogniauxia* sp. | 3 | 3 |
| *Nigrospora* sp. | 3 | 3 |
| *Peyronellae* sp. | 5 | |
| *Drechslera* sp. | 3 | |
| *Discostroma* sp. | 3 | |
| *Cochliobolus* sp. | 3 | |
| *Chaetomium* sp. | 5 | |
| *Aspergillus* sp. | 3 | |
| *Phaeosphaeria* sp. | 3 | |
| *Pyronema* sp. | 3 | |
| *Oidiodendron* sp. | 3 | |
| *Diplodia* sp. | 3 | |

TABLE 1-continued Identification and percent recovery of fungal taxa from PD-escaped and PD-infected grapevines. Results are based on sampling from 3 vineyards in Napa and Riverside County, and include 4 grapevine varieties (Merlot, Cabernet Sauvignon, Chardonnay, Riesling). Fungi were isolated from xylem sap and one-year-old cane and spur wood.

| | Percent Recovery | |
|---|---|---|
| Fungal Taxa | Escaped Grapevines (n = 37) | Diseased Grapevines (n = 30) |
| *Neofusicoccum* sp. | 3 | |
| *Epicoccum* sp. | | 7 |
| *Phomopsis* sp. | | 3 |
| *Fusarium* sp. | | 7 |
| *Cryptosporiopsis* sp. | | 3 |
| *Ulocladium* sp. | | 13 |
| *Pezizomycete* sp. | | 7 |
| *Didymella* sp. | | 3 |

Culturable fungal candidates were evaluated in an in vitro inhibition assay for antagonism against Xf. In brief, Xf liquid cultures were adjusted to $OD_{600}$ nm=0.1 (approx. 107 CFU/ml). 300 μl of the Xf cell suspension was added to 3 ml of PD3 medium containing 0.8% agar and briefly vortexed. This mixture was overlayed onto a petri plate containing PD3 medium. A #4 size cork borer was flame sterilized and used to cut out a circle of agar containing fungal mycelium from a petri plate containing a fungal culture. This circle was placed onto the plates previously inoculated with Xf. Plates were incubated at 28° C. for 10 days and then observed for an inhibition zone around the fungal colony. Measurements were taken of the inhibition zone and recorded. Fungal species with inhibition zones were considered inhibitory to Xf.

Crude extracts of the inhibitory fungi were prepared as follows. Agar plugs of 0.5 cm diameter of each fungus were used to inoculate 250 mL liquid media, and the fungi cultivated at room temperature with shaking. After 7 days, each culture was extracted with three portions of 125 mL ethyl acetate, the extracts dried over sodium sulfate, and the solvent removed in vacuo.

Xf cultures were prepared as described above. Crude extracts from the different inhibitory fungi were re-suspended in sterile ethyl acetate to a concentration of 2 mg/ml. Volumes corresponding to a total extract mass of 1 mg, 0.1 mg, and 0.01 mg were pipetted onto sterile paper discs and allowed to dry in a laminar flow hood. Once dry, the paper discs containing the crude extracts were placed onto the Xf cultures and incubated at 28° C. for 7 days. Following this, plates were observed for a halo of inhibition around the paper disc.

Grapes cuttings var. Merlot of 2 buds were vacuum infiltrated with the fungal spore suspension, planted and placed in the greenhouse. Control plants were infiltrated with sterile water only. Shoots arising from the planted cuttings were inoculated with *X. fastidiosa* (Temecula strain) by mechanical needle inoculation. A sub-sample of plants were not inoculated to determine if the concentration of fungal spores used are detrimental to the grape cuttings. Planted cuttings were evaluated for PD symptoms.

Two exemplary candidate organisms (*Achromobacter* sp. and *Geomyces* sp.) decreased PD symptom severity and Xf titer in greenhouse studies.

Initial studies demonstrated that crude ethyl acetate extracts of the culture supernatants of the biocontrol candidate *Cochliobolus* sp. possess anti-Xf activity. Using nuclear magnetic resonance spectroscopy and mass spectrometry, this inhibitory activity was traced to a single metabolite, which we identified as radicinin (a.k.a., stemphylone). Radicinin is known to be produced by several fungi, including *Cochliobolus* spp. and is also known to possess antimicrobial activity.

What is claimed is:

1. A composition comprising spores harvested from a pure culture of an endophytic microorganism selected from the group consisting of *Aureobasidium* sp., *Geomyces* sp., and a combination thereof, at a concentration of $10^5$ to $10^6$ spores/mL in sterile water; and a pure culture of *Achromobacter* sp., wherein the composition inhibits an *Xylella fastidiosa* infection in a plant.

2. The composition of claim 1, wherein the endoyphtic microorganism is *Geomyces* sp.

3. The composition of claim 2, wherein the composition is an aqueous media.

4. The composition of claim 1, wherein the plant is selected from grape, oleander, oak, almond, peach, pear, citrus, coffee, maple, mulberry, elm, sycamore, and alfalfa.

5. The composition of claim 4, wherein the plant is grape.

6. The composition of claim 1, wherein the composition is formulated for being delivered into a trunk or stem of a plant.

7. The composition of claim 1, wherein the composition is formulated to be delivered into the xylem of a plant.

8. A composition comprising a pure culture of *Achromobacter* sp.; and purified 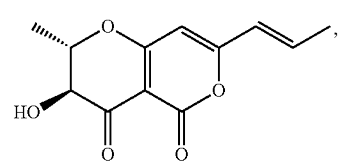 , or (Radicinin)

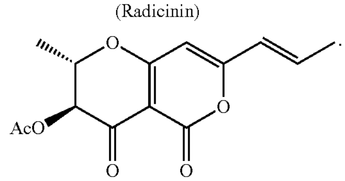

.

(acetyl-radicinin)

* * * * *